United States Patent [19]

Heilman et al.

[11] Patent Number: 4,925,443

[45] Date of Patent: May 15, 1990

[54] BIOCOMPATIBLE VENTRICULAR ASSIST AND ARRHYTHMIA CONTROL DEVICE

[76] Inventors: Marlin S. Heilman, 1016 Woodhill Dr., Gibsonia, Pa. 15044; Steve A. Kolenik, Rd. 2, Box 509, Leechburg, Pa. 15656

[21] Appl. No.: 019,701

[22] Filed: Feb. 27, 1987

[51] Int. Cl.⁵ .............................................. A61N 1/00
[52] U.S. Cl. ............................... 600/16; 128/419 PG; 128/419 D
[58] Field of Search ............... 623/3; 600/15, 16, 17; 128/64, 419 PG, 419 D

[56] References Cited

U.S. PATENT DOCUMENTS

| | | | |
|---|---|---|---|
| 3,371,662 | 3/1968 | Heid et al. | 128/24.5 |
| 3,587,567 | 6/1971 | Schiff | 128/24.5 |
| 3,668,708 | 6/1972 | Tindal | 623/3 |
| 4,048,990 | 9/1977 | Goetz | 128/64 |
| 4,167,046 | 9/1979 | Portner et al. | 623/3 |
| 4,192,293 | 3/1980 | Asrican | 128/64 |
| 4,291,707 | 9/1981 | Heilman et al. | 128/784 |
| 4,304,225 | 12/1981 | Freeman | 128/60 |
| 4,583,523 | 4/1986 | Kleinke et al. | 604/153 |

FOREIGN PATENT DOCUMENTS

| | | | |
|---|---|---|---|
| 2557475 | 6/1977 | Fed. Rep. of Germany | 623/3 |
| 2060174 | 4/1981 | United Kingdom | 128/784 |

Primary Examiner—Francis Jaworski
Assistant Examiner—G. Manuel
Attorney, Agent, or Firm—Fleit, Jacobson, Cohn, Price, Holman & Stern

[57] ABSTRACT

A device for compressing a ventricle of a heart from one or more sides in synchronism with the natural contraction of the ventricle (systole), and providing arrhythmia control of the heart, is completely implantable in the body of a patient user externally of the heart. Compression of the ventricle is produced by a plurality of spaced compression plate assemblies and a ventricle apex-compression plate, a single compression plate-band assembly or tightenable bands. The compression plate assemblies comprise suitably located electrodes for heart monitoring purposes. A power supply of the implanted device can be recharged transcutaneously, and various other components of the device can be noninvasively programmed and interrogated by external circuits. The compression plate assemblies may be operated by a small brushless DC motor. An implantable manual pump mechanism, for operating the compression plate assemblies, also is provided for emergency purposes. The components of the implanted device also include a cardiac pacer, a defibrillator/cardioverter, a recorder and an alarm.

43 Claims, 7 Drawing Sheets

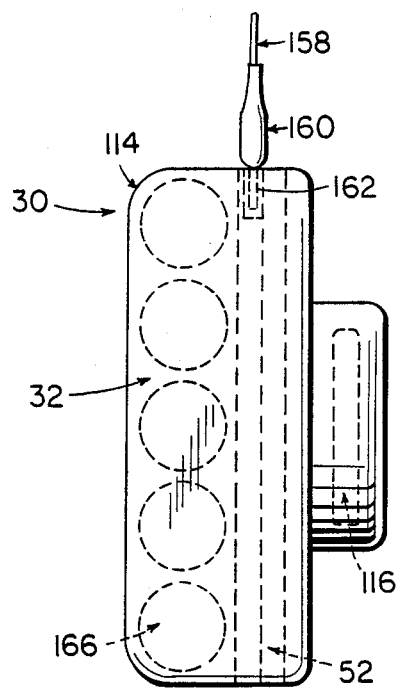
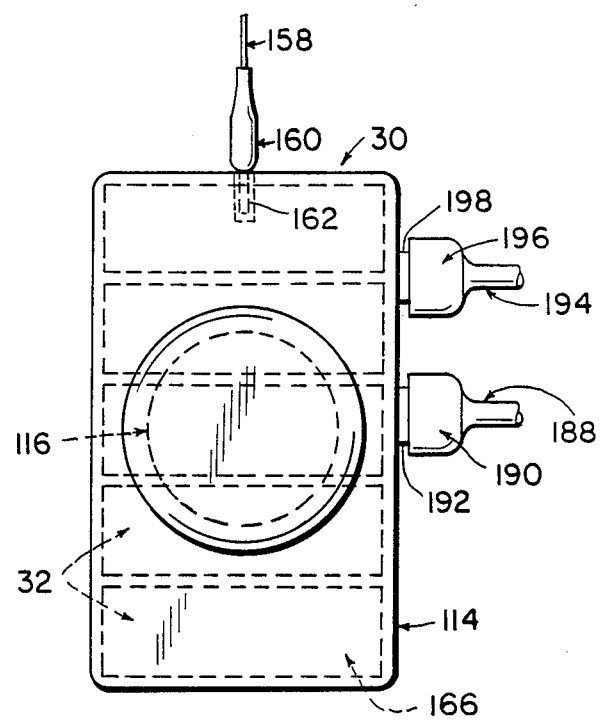
FIG. 3a
FIG. 3b
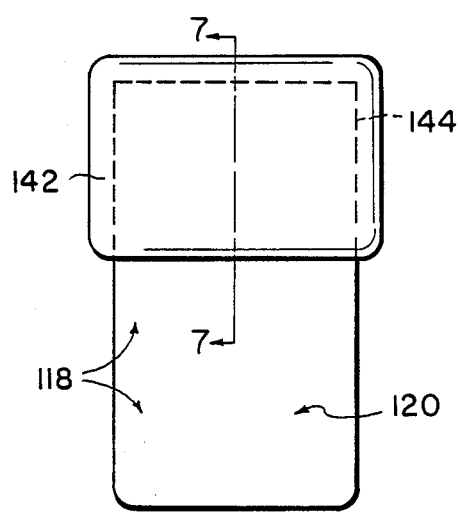
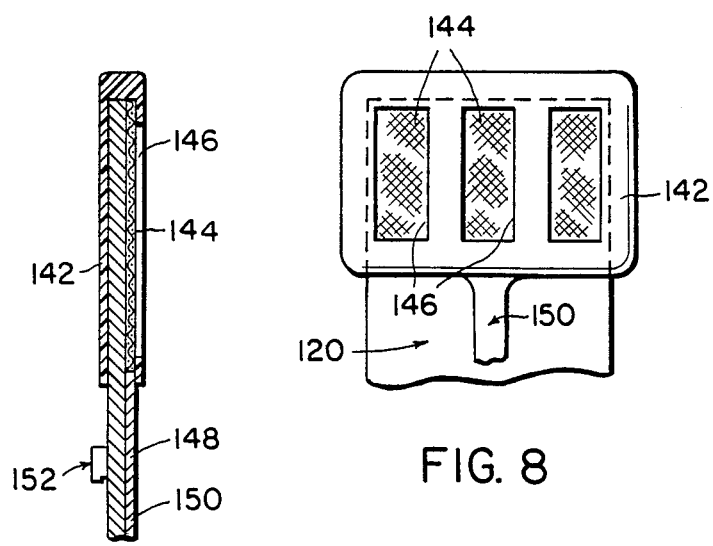
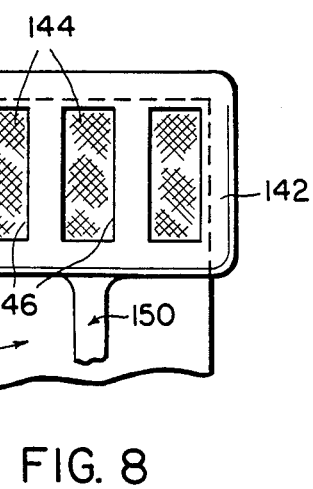
FIG. 6
FIG. 7
FIG. 8

BIOCOMPATIBLE VENTRICULAR ASSIST AND ARRHYTHMIA CONTROL DEVICE

BACKGROUND OF THE INVENTION

1. Field of the Invention

This invention relates to a biocompatible ventricular assist and arrhythmia control device, and more particularly to such a device which (1) can be completely and readily implanted external to the patient's heart, thereby avoiding thrombogenesis and other complications which may arise from contact between the blood flow and artificial, nonbiological surfaces; (2) is of relatively simple, light-weight, and compact construction; (3) requires a relatively small amount of energy to provide reliable, long-term support of native mechanical cardiac function; (4) contains control means to determine if left ventricular stroke volume and/or pressure is adequate and to change the compressive force as needed, thereby assuring an adequate flow of oxygenated blood; (5) includes bradycardic and tachyarrhythmic (pacing and cardioverting/defibrillating) control features, which will facilitate device operation in synchronism with left ventricular contraction; and (6) further enhances the patient's quality of life by providing transcutaneous recharging of the implanted power source and by maximizing the time spent free of the device's external battery pack.

2. Description of the Prior Art

The need for an improved ventricular assist device has long been apparent. The pool of patients suffering from congestive heart failure (CHF), a progressive disease often precipitated by acute myocardial infarction, continues to grow. In 1983 alone the estimated incidence of CHF, in the course of which the heart's mechanical pumping action is severely compromised, was 400,000 in the United States. Some 2.3 million or more persons suffer from varying degrees of the disease, with the estimated annual death rate from mechanical cardiac dysfunction being 165,000. Individuals with worsening CHF who otherwise would be expected to have years of productive life ahead of them, are generally regarded as candidates for a ventricular assist system. At present, however, no generally recognized safe and effective assist device is available.

Another patient group potentially in need of mechanical heart assistance consists of cardiac surgery patients who otherwise would die from profound refractory heart failure after removal of cardiopulmonary bypass. The intra-aortic balloon has been used to assist the circulation mechanically when other therapies have failed to allow weaning from cardiopulmonary bypass. However, half of these assisted patients die from cardiogenic shock (heart failure) despite the intra-aortic balloon. Therefore, a need exists for a more effective form of mechanical circulatory support that is capable of maintaining the systemic circulation and unloading the left ventricle while native myocardial function recovers.

A third patient group requiring mechanical heart assistance are those tachyarrhythmia patients who are at risk of sudden death due to electrical cardiac dysfunction but who also are at risk from mechanical heart failure.

In sum, it is estimated that a safe and effective implantable heart assist device could save the lives of 100,000 or more patients a year; some estimates go as high as 230,000.

In most cases, the underlying causes of the heart's weakened condition are coronary artery disease and its sequelae. The majority of these patients have a normal right ventricle but a left ventricle that has been damaged in specific regions by partial or complete arterial blockages. Ideally, then, a device designed to assist the failing heart should be able to supplement the heart's workload and also compensate for or support weakened portions of the left ventricular wall, including the apex or interventricular septum. Such a device might also incorporate pacemaker and implantable cardioverter/defibrillator technology for treating those patients who also suffer from such electrical dysfunctions as bradycardia or tachyarrhythmias.

Present ventricular assist devices (VADs) and artificial hearts have not met these needs. Existing devices generally feature blood flow pathways made from nonbiological materials. These materials (e.g., acrylics, TEFLON (polytetrafluorethylene), silicone rubber) often damage blood cells and blood proteins and produce clots, thereby presenting a generic risk of downstream lodgment (thromboembolism) in the circulatory system; attempts to coat plastics with heparin, an anticoagulant, have not been successful on a long-term basis. In fact, blood clots cause most of the deaths reported after implantation of an artificial heart or assist device. Depending on where lodgment occurs, blood clots may cause strokes, kidney failure, death (necrosis) of the intestinal wall or peritonitis, or equally severe damage to other organs.

In addition, cardiac arrhythmias may develop during ventricular assistance and adversely affect blood flow. Present assist devices do not treat these electrical dysfunctions. Other problems with existing assist devices include their substantial weight and the fact that they displace a large volume in the patient's body, which complicates implantation and increases the risk of other complications.

Another significant difficulty involves energy supply and consumption. Because current VADs lack a satisfactory implantable energy source, they must be continuously powered percutaneously. This produces a high risk of infection and generates psychological problems for the patient, who must be constantly tethered to an external power source. Some VADs now under development may offer rechargeable implanted batteries coupled with continuous electromagnetic energy transmission through the skin, the external energy source being a series of nickel cadmium batteries placed in a vest or belt. Other state-of-the-research-art VADs may allow the patient to remove the vest or belt for a brief period—up to 20-30 minutes, for example. However, greater freedom from external device dependence continues to be constrained because the implantable batteries used in these devices have a limited number of recharge cycles, poor state-of-charge indicators, poor energy density, and poor energy retention, particularly at body temperature.

Previous attempts to provide ventricular assistance have ranged from artificial hearts (e.g., the Jarvik-7), to devices which directly pump the blood via an artificial pathway inserted through the ventricular wall, to devices which exert pressure on the outside of the heart. Most frequently, pressure-exerting devices involve some form of flexible bladder within a support structure such that expansion of the bladder presses on the ventricle and facilitates expulsion of blood. See, for example, U.S. Pat. Nos. 3,587,567 to Schiff; 3,371,662 to Heid et al.; 4,048,990 to Goetz; and 4,192,293 to Asrican. Another structurally related device (U.S. Pat. No. 4,506,658 to Casile) envisions a truncated conical structure of sac-lined rigid panels separated by contractible and expandable sections.

In all of these proposed devices, the support structure encases all or most of the heart and either pushes against or otherwise contacts the right as well as the left ventricle. This complicates ventricular assistance since most cases of heart failure are due to a failure of the left ventricle, not the right. The right ventricle, which pumps against a pressure that is typically one-fifth of that seen by the left, is generally capable of proper function without assistance. Accordingly, these devices risk preferentially pumping blood from the right ventricle, as a consequence of which blood would accumulate in the lungs and cause pulmonary edema. In recognition of this difficulty, one recent proposal (U.S. Pat. No. 4,536,893 to Parravicini) envisions using two segmented sacs, selectively fed by a pumping fluid, to compress the ventricles separately.

Bladder systems have additional shortcomings. These include the possibility of catastrophic bladder fluid leakage, a propensity for damaging the heart surface due to poor fixation and/or rubbing of the bladder against the heart's surface, and the unnatural convex form presented to the heart's surface during systolic bladder expansion.

Another type of cardiac assist system is designed to compress all or part of the heart by alternately tightening and releasing a circumferential compression band. For example, one proposed system for body organs (U.S. Pat. No. 4,304,225 to Freeman) involves a flexible strap which is fixed to a contoured plastic block and which would pass across the back of the heart. In response to electrical pulses, a motor assembly would alternately reel in and release the flexible strap, thereby forcing fluid from the subject organ. One liability of this approach is that a pressure of between 20 and 70 mm Hg in the volume under the strap would pump blood from the right ventricle but not the left, since 70 mm Hg or more is required for blood to exit the left ventricle into the aorta. As with the bladder-type devices discussed above, such a preference could lead to a buildup of blood in the lungs, producing severe pulmonary complications.

U.S. Pat. No. 4,583,523 to Kleinke and Freeman illustrates a heart assist mechanism with some similarities to the present invention. However, there are numerous differences. For example, Pat. No. 4,583,523 compresses the aorta, not the left ventricle, and it compresses during the diastolic phase of cardiac contraction instead of the systolic phase. Furthermore, it has no means to continuously control the depth of stroke. Specifically, there is no means to monitor the adequacy of left ventricular stroke volume.

SUMMARY OF THE INVENTION

This invention relates to an implantable ventricular assist device which includes (1) one or more movable compression mechanisms for engaging the left ventricle of the heart; (2) an operating mechanism for cyclically actuating the movable compression mechanisms and thereby alternately ejecting blood from the ventricle and permitting the ventricle to refill; (3) a sensing means to detect adequacy of left ventricular stroke volume and/or pressure; (4) a control mechanism to assure adequate left ventricular stroke volume by regulating the compressive force of the compression mechanisms, and also to control pacemaker, cardioverter/defibrillator, and recorder subsystems; and (5) an electrical power source.

More specifically, compression mechanisms for engaging the sides of the left ventricle may be spaced triaxially. A typical configuration would have three compression assemblies placed in the anterior, lateral, and posterior positions with respect to the left ventricle; viewing the left ventricle from the base of the heart and positioning the midpoint of the right ventricle at 270°, typical midpoints for the three compression assemblies would be 190°, 90°, and 350°.

Each compression mechanism includes a contoured pressure plate and a soft contact pad mounted on the interior plate surface for suturing and/or gluing the compression mechanism to the ventricle. An examination of explanted cardiomyopathic hearts suggests that the typical compression assembly surface should be 4–5 cm long and should be tapered (wider at the top, narrower at the bottom), thereby reflecting the shape of the ventricle. Each compression mechanism should cover approximately 70° of circumferential arc.

To minimize mechanical stress on the myocardial surface, including the coronary arteries, the contact pad consists of an elastomer, such as silicone rubber, or a thermoplastic material (durometer range 30–50). To avoid edge stress, the thickness of each contact pad is progressively reduced toward its periphery. To further reduce stresses on the myocardium, bearings and axles are used to mount the pressure plates on the compression mechanism's driving arms: if the contracting heart produces a torquing force, the joint will permit the pressure plate, within specified limits, to follow the natural movement of the heart.

In those few cases where the right ventricle also needs assistance, the triaxial compression mechanisms may be supplemented by a fourth, smaller mechanism positioned on the right ventricle. As another option, a smaller apical pressure plate may be added. Alternatively, one or more compression mechanisms may cooperate with a tension band surgically placed through the interventricular muscle wall of the heart; the opposite ends of the tension band would be connected to a rigid support external to the heart, with one or more pressure plates positioned between the block and the heart. In a further variation, the tension bands would be rigidly fixed to the compression mechanisms, which, when closed by the operating means, would reduce the circumference of the band opening and thereby squeeze the heart.

The operating mechanism, for cyclically actuating the compression mechanisms, includes a motor for inducing controlled reciprocating motion plus a means for mechanically translating this motion into pressure-plate compression. The invention includes a brushless, battery-powered D.C. motor which utilizes an annular energizing coil and magnets to drive a roller screw. The roller screw engages a bellows pusher (or a similarly functioning component, such as a rolling diaphragm), which in turn is connected, via fluid-filled elastomeric tubing, with a compression housing that contains a second bellows. When pressure is exerted on the first bellows by the roller screw, the fluid coupling transmits pressure to the second bellows, to which is attached a driving wedge that engages the mounted compression mechanisms and thereby aids ventricular compression.

The fluid coupling permits the cylindrical motor housing to be implanted in a posterior mediastinum position parallel to the descending aorta, while the pumping mechanism housing is positioned in the left chest, adjacent the left ventricle. In a second embodiment of this invention, the motor housing and the pumping mechanism housing would form an integral unit, with the nut of the roller screw bonded to the driving wedge. In both embodiments, linear movement of the roller screw mechanically governs the degree of pressure-plate movement (compression and return) in the compression axis.

To allow the pumping mechanism housing (first embodiment) or the integral motor/pump housing (second embodiment) to float with the natural movement of the heart, the assembly may be placed in a lubricant-filled sac. At the same time, tethering the assembly to, for example, the ventral surface of the sac would limit the degree of motion.

The implanted, programmable control mechanism, for regulating actuation of the operating mechanism, utilizes input provided in part from device motion sensors, an arterial blood pressure sensor, blood flow sensors, heart rate-sensing (R-wave sensing) electrodes, and/or ECG morphology-sensing electrodes positioned in the heart and/or on the compression mechanisms. The associated pacemaker unit, implantable cardioverter/defibrillator and energy storage device, transcutaneous programmer/interrogation unit, and internal biological recorder are of types known to those skilled in the art.

Further, the transcutaneous power supply is also of a type known to those skilled in the art. The implanted electrical source is a pack of high-energy rechargeable batteries and a pickup coil disposed in a biocompatible casing capable of subcutaneous placement. In addition to providing energy to the control, operating, and compression mechanisms, device circuitry may also produce and conduct pacemaker pulses and/or cardioverting/defibrillating pulses via the above-mentioned electrodes.

Also, a manually operated mechanism may be provided for moving at least one pressure plate to compress the left ventricle in the event of a device malfunction; sensors may be included in the control mechanism for sensing such malfunctions.

An object of the invention is to provide a new and improved biocompatible ventricular assist device which (1) can be completely and readily implanted in the patient's body, external to the heart and to blood flow pathways; and (2) is relatively simple, light-weight, and compact.

An additional object of the invention is to provide compression means which minimize trauma of the myocardial surface due to repeated artificial compression.

An additional object of this ventricular assist device is to maximize the contribution of native left ventricular function, thereby maintaining the myocardium in an exercised state while increasing device efficiency and further lengthening the interval between rechargings.

Another object of this invention is to provide such a ventricular assist device which also treats electrical dysfunctions (atrial and ventricular, bradycardic and tachyarrhythmic) to facilitate synchronous pumping, thereby assuring an adequate flow of oxygenated blood.

A further object of this invention is to consume a relatively small amount of electrical energy for mechanical operation, thereby permitting the invention to function for a relatively long period of time between transcutaneous rechargings of the implanted power source.

Another object of the invention is to provide reliable operation over a relatively long time period, such as a minimum of 5-10 years.

Yet an additional object of the invention is to provide reliable operation over a large number of cycles.

An object of this invention is also to provide means for transcutaneous programming of operating parameters and transcutaneous interrogation as to prior operations.

An additional object of the invention is to provide a failsafe mechanism whereby the compression means, in the event of device failure, does not restrict natural movement of the epicardium and whereby the device can be manually operated by the patient user or another individual.

BRIEF DESCRIPTION OF DRAWINGS

FIG. 2b is a schematic general plan view as seen along the line 2b—2b in FIG. 2a;

FIG. 3a is a schematic front view of an electronic module for the device;

FIG. 3b is a schematic side view of the electronic module shown in FIG. 3a;

FIG. 4c is a top view as seen along the line 4c—4c in FIG. 4a;

FIG. 4d is an enlarged cross-sectional view of a drive mechanism in accordance with the first embodiment of the invention, taken generally along the line 4d—4d in FIG. 2a;

FIG. 5b is a top view as seen along the line 5b—5b in FIG. 5a;

FIG. 6 is a side view of an upper portion of a ventricular compression mechanism of the ventricular assist device;

FIG. 7 is a cross-sectional view of a portion of the ventricular compression mechanism shown in FIG. 6, taken along the line 7—7;

FIG. 8 is an opposite-side view of a portion of the ventricular compression mechanism shown in FIG. 6;

DETAILED DESCRIPTION

Figure 1:
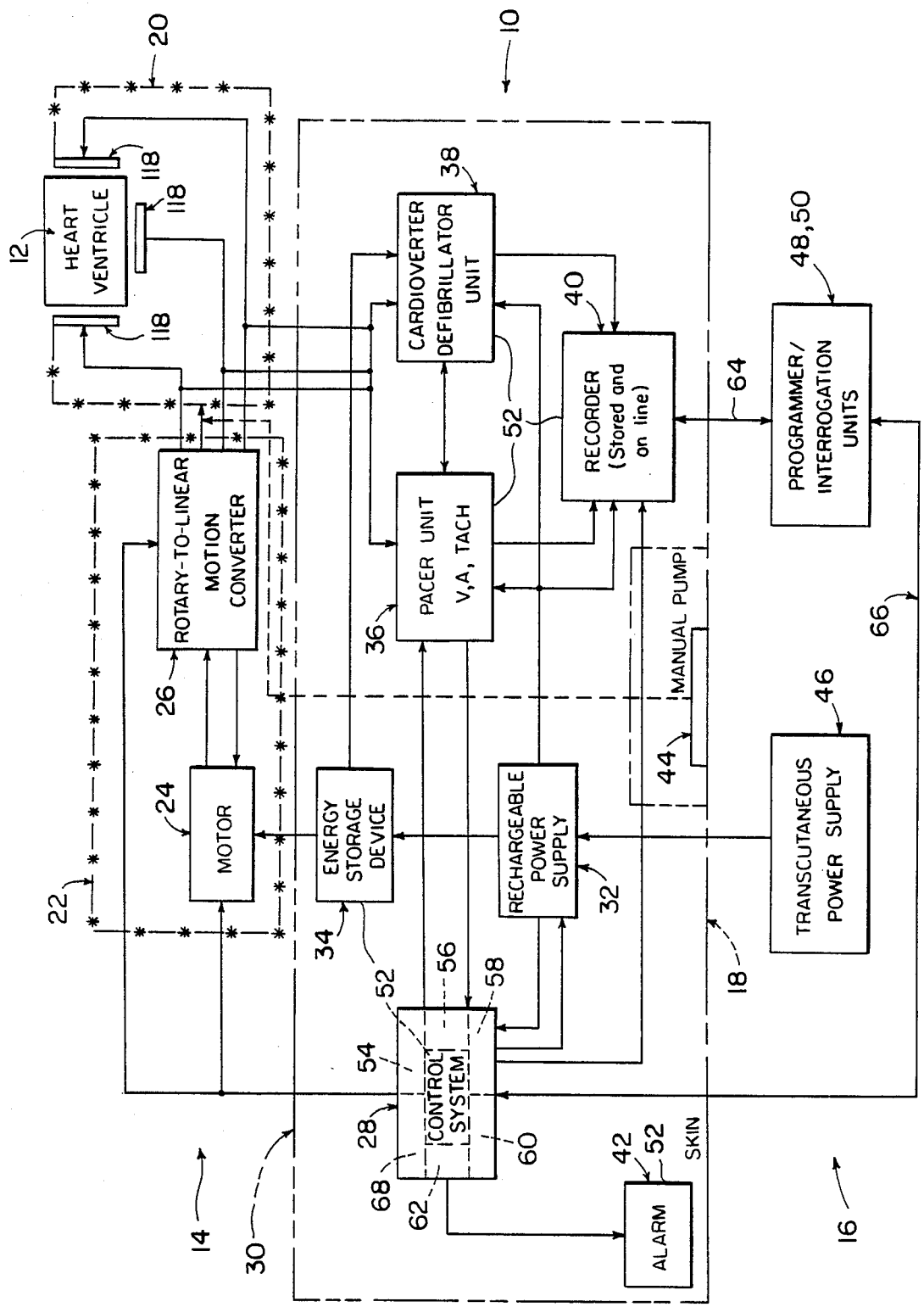
FIG. 1 is a schematic block diagram of a first embodiment of a ventricular assist device in accordance with the invention.

FIG. 1 discloses a block diagram of one embodiment of a biocompatible ventricular assist and arrhythmia control device 10 in accordance with the invention, hereafter referred to as the ventricular assist device, it being understood that numerous other variations of the invention are, of course, possible. As disclosed in FIG. 1, the ventricular assist device 10, which operates, on demand, in synchronism with a heart left ventricle 12, comprises an implantable subsystem 14 and a subsystem 16 external to, and without penetrating, a patient user's skin 18. The implantable subsystem 14 includes a direct cardiac pumping mechanism 20 and a motor housing 22, both outlined by alternating dashes and asterisks. The motor housing 22 includes a motor 24 and a rotary-to-linear motion converter 26 which mechanically initiates (directly or indirectly) the inward ventricle-assist motion of the pumping mechanism 20 when the left ventricle 12 begins to contract, limits and controls the degree of mechanical compression, and terminates the compression stroke so that the pumping mechanism 20 may return to its original outward position as the ventricle refills. The pumping mechanism 20 and motor housing 22 also include sensors which provide input to a device control system 28, within an electronic module 30.

The electronic module 30, as indicated in broken lines, includes, in addition to the control system 28, a rechargeable power supply 32 and an energy storage device 34, which may be one or more capacitors. The electronic module 30 further includes a cardiac pacer unit 36 and a cardioverter/defibrillator unit 38 for arrhythmia control, in part to promote operation of the pumping mechanism 20 in synchronism with the left ventricle 12; a biological signal recorder 40; and a patient alarm device 42. Another feature of the implantable subsystem 14 is an emergency manual pumping mechanism 44, located outside the electronic module 30 and connected to the direct cardiac pumping mechanism 20.

The external subsystem 16 includes a power supply 46, for charging the internal power supply 32 transcutaneously, and noninvasive combined programmer/interrogation units 48, 50.

Figure 2A:
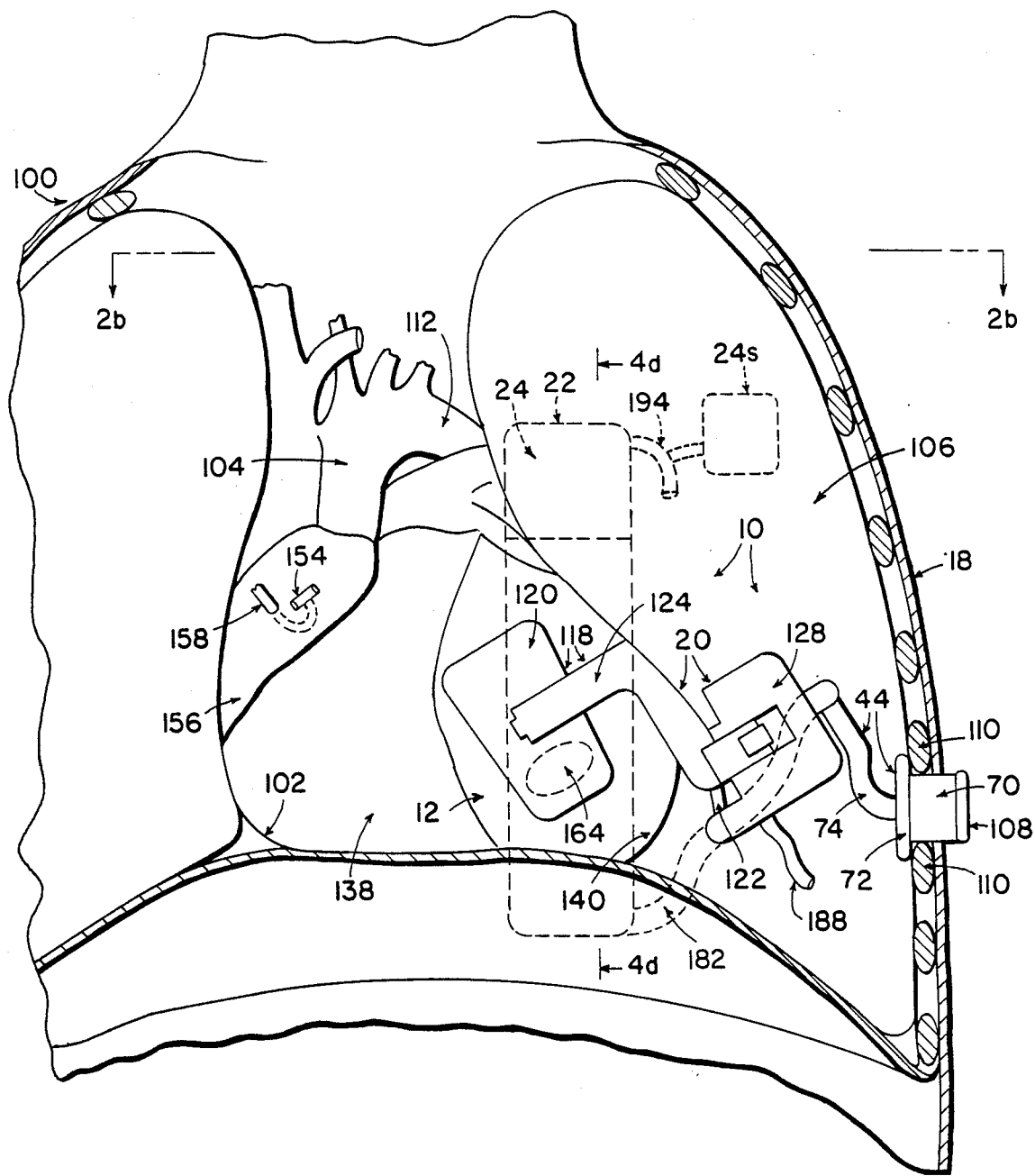
FIG. 2a is a schematic general front elevational view of the upper portion of a human body in which is implanted the first embodiment of the ventricular assist device in accordance with the invention.
Figure 2B:
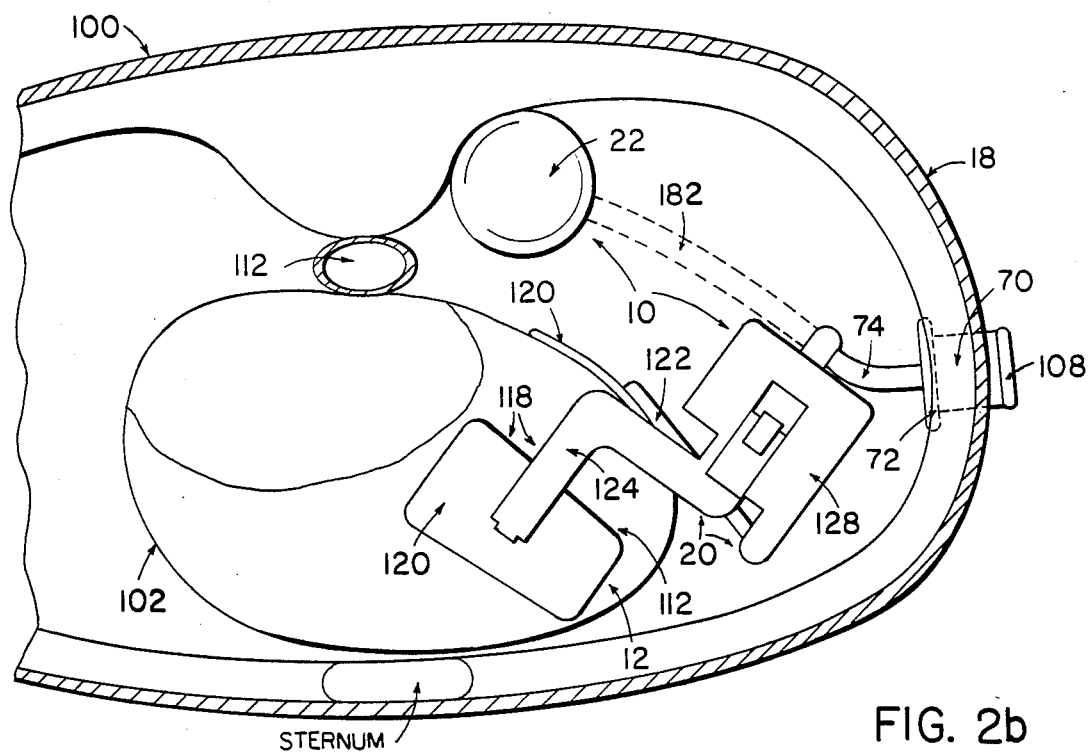

FIGS. 2a and 2b show the ventricular assist device 10, as represented by the block diagram of FIG. 1, implanted in an upper portion of a human body 100 for assisting the left ventricle 12 of a heart 102 in the pumping of blood from the heart, through the aorta 104, and to the arterial system. It is to be understood that the disposition of the various parts of the ventricular assist device 10 as shown in FIGS. 2a, 2b and subsequent figures is merely for purposes of illustration and that other location arrangements may be used.

The pumping mechanism 20 (FIG. 2a) engages the walls of the left ventricle 12 and is disposed in part between the left ventricle and the left lung 106. A manually operable button 108 of the manual pumping mechanism 44 is positioned between two adjacent ribs 110, with the button protruding under the skin 18 to facilitate emergency use by the patient user or by another person. The cylindrical motor housing 22 (in outline) of the ventricular assist device 10 is disposed in a posterior mediastinum position parallel to the descending aorta 112.

As shown in FIGS. 3a and 3b, the electronic module 30 and rechargeable power supply 32 are combined in a single casing 114 which may be implanted in a subcutaneous abdominal pocket or inside the rib cage, in which case an energy pickup coil 116 of the rechargeable power supply 32 may be positioned subcutaneously between two adjacent ribs 110 (FIG. 2a).

Figure 4D:
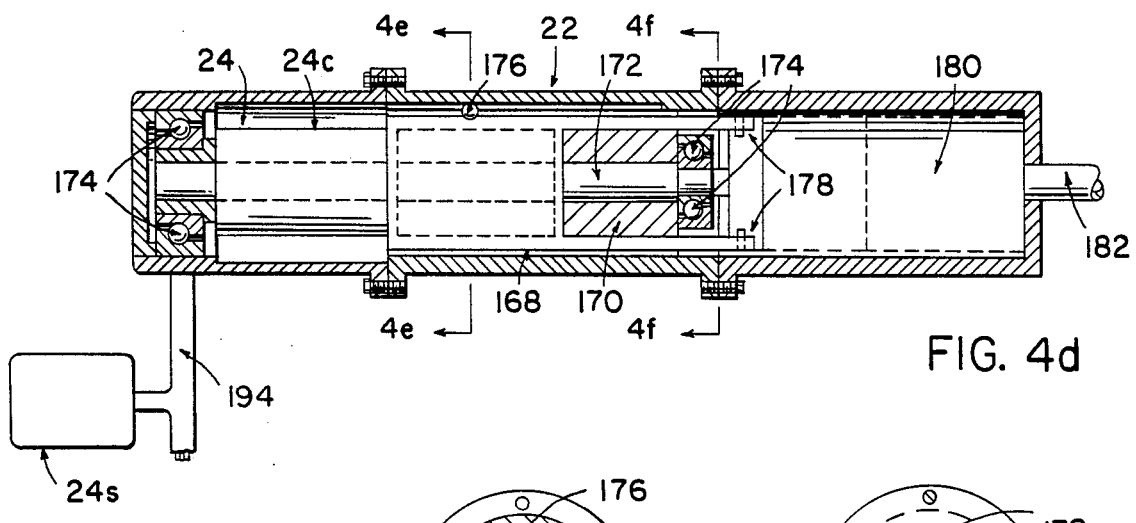
Figure 4E:
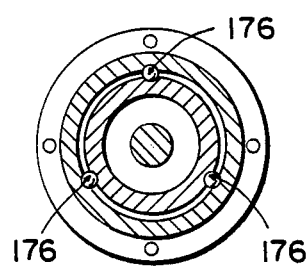
FIG. 4e is a view partially in cross-section, taken along the line 4e—4e in FIG. 4d.
Figure 4F:
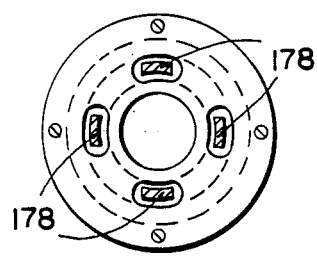
FIG. 4f is a cross-sectional view taken along the line 4f—4f in FIG. 4d.
Figure 4A:
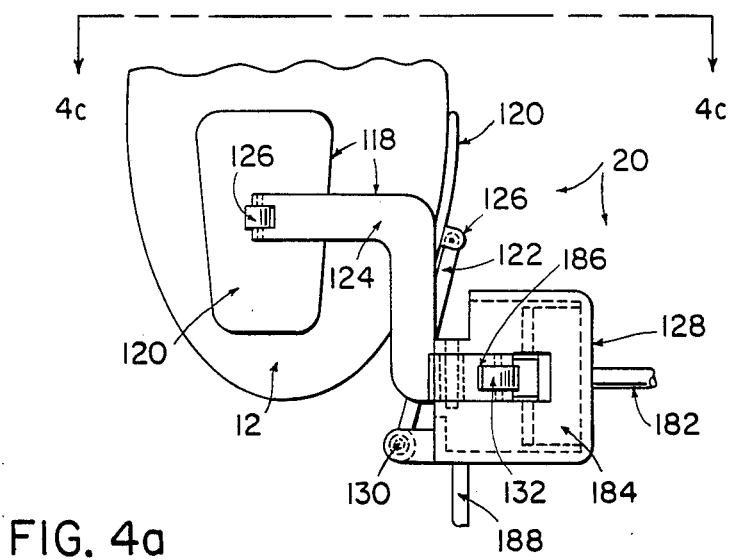
FIG. 4a is an enlarged front elevational view of a direct cardiac pumping mechanism of the first embodiment of the invention.
Figure 4B:
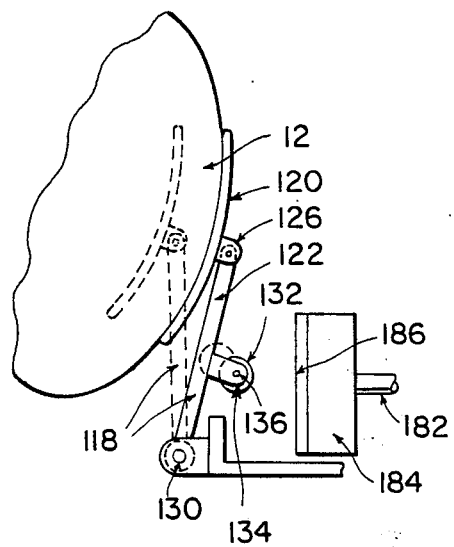
FIG. 4b is a separate front view of a part of the pumping mechanism shown in FIG. 4a, illustrating first and second operating positions.
Figure 4C:
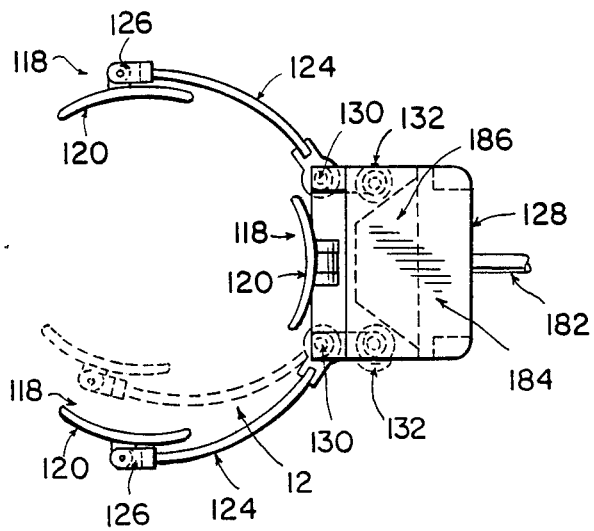

As is best shown in FIGS. 4a, 4b and 4c, the pumping mechanism 20 includes triaxial lateral pressure plate assemblies 118 around the heart 102, for engaging and compressing the left ventricle 12 in synchronism with native or pacemaker-initiated pumping action. Each pressure plate assembly 118 includes a pressure plate 120 formed of a spring-tempered, biocompatible, inert metal, such as the nickel alloy MP35NR (an alloy of nickel, cobalt, chromium, and molybdenum). Each pressure plate 120 is attached to a driver arm 122 or 124 by way of an axle/bearing mount 126 so that the pressure plate may follow, within specified limits, the natural movement of the heart. Each driver arm 122 or 124 is mounted on an actuator housing 128, pivoting on a light-weight, high-performance bearing 130, which, like the bearing in the axle/bearing mount 126, consists of a tubular lining of woven Teflon/Dacron fabric and an inner wound fiberglass epoxy resin matrix. The driver arms 122 and 124 and the actuator housing 128 consist of a biocompatible metal compound, such as Ti6A14V (titanium, aluminum, and vanadium). Driver arms 122 and 124 are engaged by wedge followers 132, each of which includes a roller 134 mounted on a follower bearing 136 (of similar construction to arm bearing 130).

The above pumping or compression mechanism 20 is readily adapted to varying combinations of pressure plate assemblies 118. For example, triaxial lateral placement could be supplemented with a fourth, smaller plate (not shown) positioned on the right ventricle 138 (FIG. 2a), or with an apical plate (not shown) for supporting and supplying compressive force to the left ventricular apex 140.

Figure 5A:
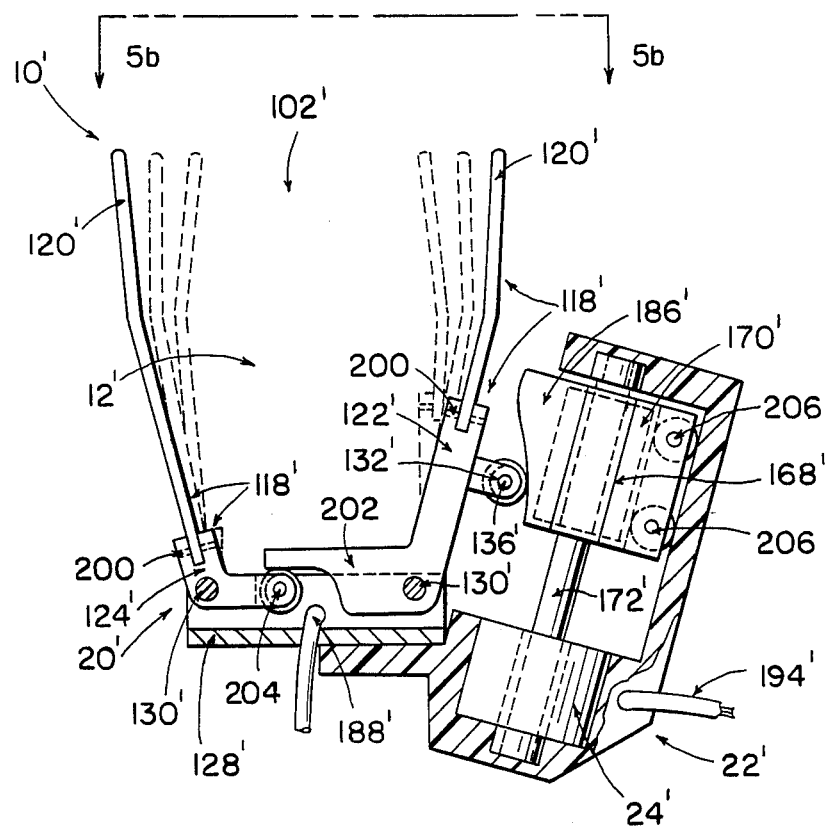
FIG. 5a is a cross-sectional front elevational view of a portion of a second embodiment of the invention.
Figure 5B:
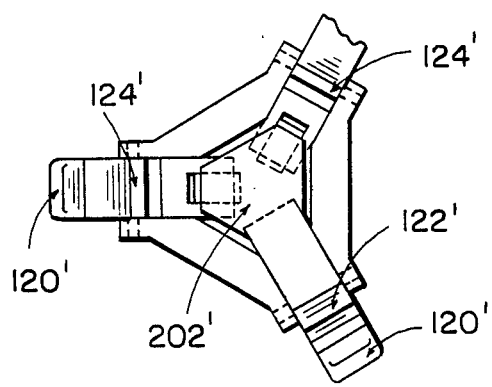

It should also be perceived that other embodiments of the pumping mechanism 20 are possible. For example, in a second embodiment of the ventricular assist device 10', as illustrated by FIGS. 5a and 5b, a pumping mechanism 20' includes triaxial lateral pressure plate assemblies 118' (only two shown in FIG. 5a) around the heart, with the upper portion of each pressure plate 120' adjoining the left ventricle 12' and the lower portion extending downward into a driver arm 122' or 124' (two of the latter) to which it is fastened by a set screw 200. Driver arm 122' differs from driver arms 124' in that its associated pressure plate assembly 118' is shorter, while its upper extension is correspondingly longer to accommodate wedge follower 132'. Driver arm 122 also differs in that its lower extension includes a six-sided rocker plate 202, which extends over housing bearings 204 (one shown) to which each driver arm 124' is also fixed.

The pressure plates assemblies 118 (FIGS. 4a, b and c) are movable between solid line positions when the left ventricle 12 expands (diastole) and broken line positions (FIGS. 4b and 4c) when the left ventricle contracts (systole). Strain relief sensors (not shown) may be incorporated on the pressure plates 120 to assure that the pumping mechanism 20 does not restrict filling of the left ventricle 12 and does not assist compression unless natural compression is inadequate.

Referring to FIGS. 6, 7, and 8, each pressure plate assembly 118 also includes a contact pad 142 for gluing and/or suturing the pressure plate assembly to the left ventricle 12. The contact pad 142 is bonded to an upper portion of each pressure plate 120 by an adhesive, with both the contact pad and the adhesive consisting of electrically insulating materials, such as a silicone rubber (reinforced with DACRON (polyester) fibers, in the case of the pad) or a thermoplastic. In addition, the contact pad 142 has a thickness which is progressively reduced toward its periphery to avoid edge stress, and is soft enough (durometer range 30-50) to minimize the possibility that pressure from the pressure plate assemblies 118 would damage cardiac muscle or the coronary arteries, or would interfere with the muscle's blood supply. (It should be noted that most of the heart muscle's blood supply is delivered during diastole, when minimal force is exerted by the pressure plates 120.)

Each contact pad 142 includes a rectangular electrode 144 bonded by an electrically insulating adhesive (e.g., a silicone rubber), both to the ventricle-engaging surface of the contact pad 142 and to the pressure plate 120. To enable the electrode 144 to make direct contact with heart tissue, the ventricle-engaging surface of the contact pad 142 contains openings 146, as is best shown in FIG. 8. Each electrode 144 is connected to the electronic module 30 (FIGS. 3a and 3b) via conductors 148 (one shown in FIG. 7) that are contained by a cable 150 bonded to one side of the pressure plate 120 and extending downward to the actuator housing 128. Thus monitoring and control signals are transmitted to and from the electrodes 144, which may be formed of any suitable material, such as titanium wire mesh.

Referring again to FIG. 7, for purposes of cardiac monitoring a set of bipolar spaced electrodes 152 also is provided on at least one of the pressure plate assemblies 118. The electrodes 152 are supported on the pressure plate by an adhesive, such as a silicone rubber, and are connected to respective conductors of the cable 150. Another, J-shaped bipolar electrode 154 (FIG. 2a) is implanted in or near the right atrium 156 of the heart 102 and is connected to the electronic module 30 (FIGS. 3a and 3b) by insulated conductors 158 (only one shown); the connection means may include, for example, a plug 160 that mates with a socket 162 in the electronic module 30. The spaced bipolar electrodes 152 and 154 each have an interelectrode spacing of 1-2 centimeters and may be formed of platinum or platinum-iridium.

Under normal conditions, contraction of the left ventricle 12 can be properly assisted by compressing the pressure plate assemblies 118 approximately 0.46-0.50 inches (1 centimeter). Although cineangiography studies indicate that the requisite compression distance is relatively independent of heart size, different heart sizes can be accommodated by increasing (or decreasing) the thickness of the contact pads 142 and by selecting larger or smaller plates 120. In addition, the compression mechanism 20 has been designed such that a one centimeter stroke can be accomplished within a start-stop range of two centimeters; this permits the position of the pressure plate assemblies 118 to be adjusted to accommodate a range of heart sizes.

The ventricular assist device 10 is particularly useful if the heart's left ventricle 12 has been damaged by scarring. As illustrated in FIG. 2a, a thin area of scar tissue 164 has formed on the ventricle's ventral wall, replacing contractile muscle. This thinning of the cardiac tissue is a common cause of weakened left ventricular function. Not only is the scar tissue 164 unable to contract, it may actually bulge outward during systole, absorbing the energy of contraction from the functioning muscle tissue. Accordingly, by positioning the contact pad 142 of a pressure plate assembly 118 over the scar tissue 164, outward bulging of the thin wall during systole is prevented and proper contraction is achieved.

As shown in FIG. 4d, the motor housing 22 includes a brushless DC motor 24 that drives the pumping mechanism 20 (FIG. 4a). It operates directly from rechargeable batteries 166 in the electronic module 30 (FIGS. 3a and 3b) and includes an annular energizing coil 24a which surrounds an annular series of permanent magnets (not shown). The permanent magnets consist of neodymium, iron, and boron (Nd2Fe14B), or similar materials, for maximum efficiency and reliability as well as minimum weight. An energizing field is applied to the permanent magnets in sequence to drive a roller screw device 168 which converts rotary motion to linear motion. The roller screw device 168 may, of course, be replaced with a different type of linear actuator (e.g., a ball screw or a set of appropriate gears), if so desired.

The brushless DC motor 24 may be of a type available on a custom design basis from Sierracin/Magnedyne, of Carlsbad, Calif. With such a motor, the overall system efficiency (mechanical energy to blood/electrical energy from batteries) is about 60-70% or more, which is significantly higher than the 40-50% efficiency of presently known ventricular assist devices. A typical set of design parameters for the motor 24 is as follows:

| Motor: | Rated torque | 5 oz-in |
|---|---|---|
| | Rated speed | ¾ radians/sec |
| | Input current | 1.1 amperes |
| | Input voltage | 10 volts |
| | Input power | 13 watts |
| | Output power | 11 watts |
| | Efficiency | 85 percent |
| | Duty cycle | 25-50 percent |
| | O.D. | 1.25 in |
| | I.D. | 0.31 in |
| | Height | 0.87 in |
| | Weight | 70 grams |

The roller screw device 168 is also of a known type, such as that available from Rollvis S.A. of Geneva, Switzerland. It features a rotatable outer cylinder (nut) 170 that is internally screw threaded, and a reciprocating shaft 172 that is mounted in the cylinder 170 and externally screw threaded. Deep groove ball bearings 174 permit the reciprocating shaft 172 to slide, but not to rotate; this may be accomplished, for example, by interengaging splines and grooves (not shown). Another set of ball bearings 176 (Figures 4d and 4e), situated in a groove in the housing 22, are designed to absorb any torque that would otherwise be exerted on the nut 170.

Referring to FIGS. 4d and 4f, integral with the periphery of the nut 170 are four arms 178 which are extended between the bearings 174 and which are welded to one end of a bellows pusher 180. The bellows 180, like the motor housing 22, is formed from a suitable biocompatible material, such as Ti6A14V. An elastomeric tube 182 extends from the end of the bellows 180, through the end of the motor housing 22, and connects to a reciprocating bellows 184 that is contained within the actuator housing 128 (FIG. 4a). The paired bellows 180, 184 and connecting tube 182 contain a biocompatible fluid, such as mineral oil, and together constitute a fluid coupling.

Linear motion of the reciprocating shaft 172 causes the nut 170 to exert pressure upon the bellows 180, with the fluid coupling then transmitting pressure to the second bellows 184, to which is welded a driving wedge 186. In turn, the wedge 186 exerts lateral pressure on the wedge followers 132, which then cause the pressure plate assemblies 118 to pivot on the arm bearings 130 and compress the left ventricle 12 simultaneously.

The second embodiment of the ventricular assist device 10' (FIG. 5a) is similar to the preferred first embodiment except that an actuator housing 128' and a motor housing 22' are directly joined, with a driving wedge 186' permanently bonded to and surrounding a roller screw nut 170' such that a single wedge follower 132' is directly engaged upon linear movement of a reciprocating shaft 172' (downward in FIG. 5a). The wedge 186', which is also supported along the distal wall of the housing 22' by bearings 206 (of similar construction to bearings 130', 136', and 204), exerts lateral pressure on the wedge follower 132', which in turn causes a right pressure plate assembly 118' to compress the heart 102'. Collaterally, as driver arm 122' pivots on right arm bearing 130', rocker plate 202 is forced downward, exerting pressure on housing bearing 204 and causing the driver arms 124' to pivot on their respective arm bearings 130'. As a result, all three pressure plate assemblies 118' compress the left ventricle 12' simultaneously. It is also contemplated that the coupling of a motor 24' and the roller screw shaft 172' could be achieved by a magnetic clutch so that in the event of power failure the pressure plate assemblies 118', like those of the preferred embodiment, would present no resisting force to the left ventricle 12'.

To allow the cardiac pumping mechanism 20 (or combined pumping mechanism/motor housing 20', 22') to float with the natural movement of the heart, they may be placed in a lubricant-filled sac (not shown). At the same time, tethering the assembly to the ventral surface of the sac would limit the degree of motion.

Figure 9:
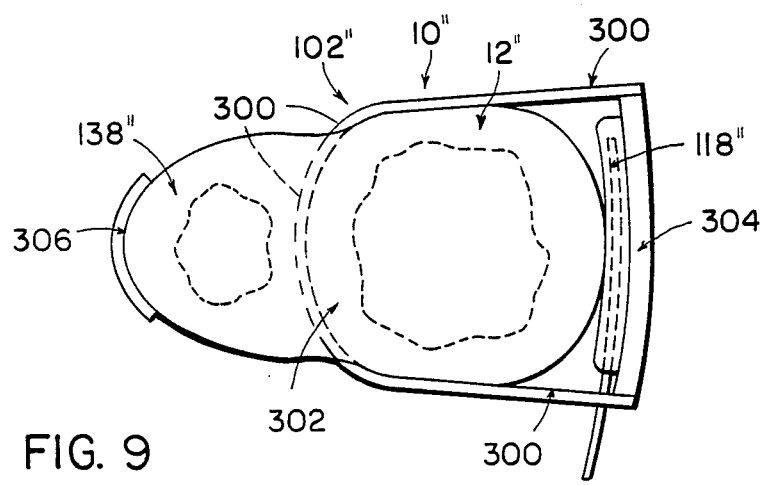
FIG. 9 is a schematic view of a third embodiment of the invention in a first operating position.
Figure 10:
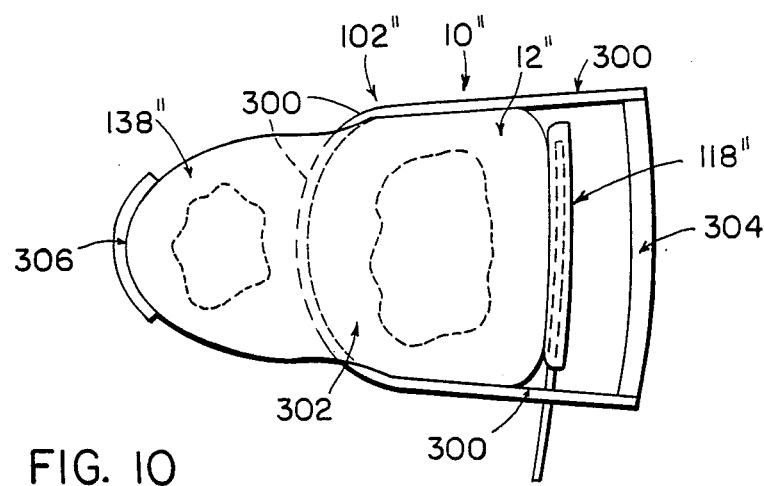
FIG. 10 is a schematic view showing the embodiment of FIG. 9 in a second operating position.

In the embodiment of the invention as shown in FIGS. 9 and 10, a ventricular assist device 10" includes a pressure plate assembly 118" positioned on a lateral wall of a left ventricle 12" of a heart 102". However, instead of the pressure plate assembly 118" being opposed by other left ventricular pressure plate assemblies, an intermediate portion of a titanium or platinum tension band 300 is surgically placed in an interventricular muscle wall 302 between the left ventricle 12" and a right ventricle 138". Opposite ends of the tension band 300 are fixed to a rigid support (e.g., a curved plate) 304 implanted in adjacent body tissue so as to be essentially immovable. A separate defibrillating electrode 306 is mounted on the outside of the right ventricle 138", for providing cardioverting/defibrillating current to the inner surface of the pressure plate assembly 118".

FIG. 10 illustrates the action of the ventricular assist device 10" when the pressure plate assembly 118" is moved to the left by a pumping mechanism of the type shown in FIGS. 4a or 5a. The pressure plate assembly 118" and the rigid structure 304 separate, resulting in constriction of the left ventricle 12" during ventricular contraction. The advantage of this embodiment of the invention is that it compensates for weakness of the interventricular muscle wall 302 and, by encompassing the ventricle 12", gives generalized support to the contracting ventricle.

Figure 11:
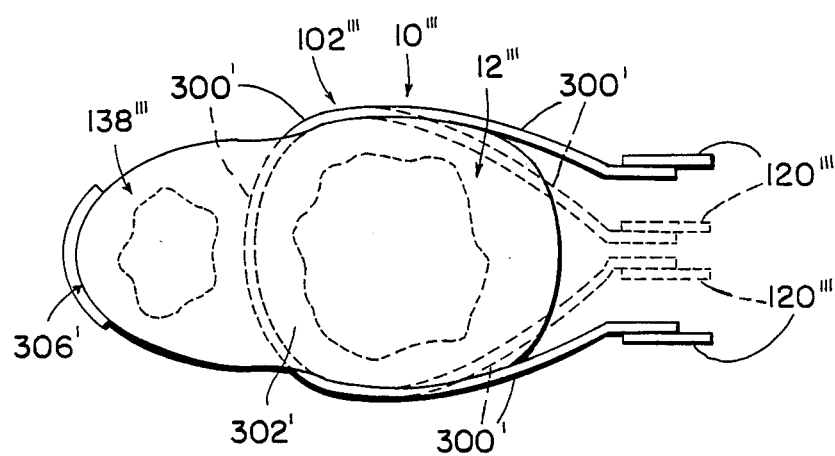
FIG. 11 is a schematic view of a fourth embodiment of the invention.

In the further embodiment of the invention shown in FIG. 11, a ventricular assist device 10'" includes one or more encircling bands 300' (only one shown) positioned around, for example, a left ventricle 12'". As in FIGS. 9 and 10, intermediate portions of the bands 300' are surgically implanted in an interventricular wall 302' between the left ventricle 12'" and a heart right ventricle 138'". Further, opposite ends of the bands 300' are connected to a suitable operating mechanism by being rigidly fixed (e.g., welded) to two pressure plates 120'". Thus, when the pressure plates 120'" close, the bands 300' are moved from solid to broken line positions, thereby compressing the left ventricle 12'".

With specific reference to FIGS. 3b, 4a, 4d, and 7, an electrical conductor conduit or cable 188, which may be bonded to the actuator housing 128 (as in FIG. 4a), includes a multipin connector 190 (FIG. 3) at its free end, which connects with a mating plug 192 that is mounted on the casing 114 of the electronic module 30. The conduit 188 houses all electrical conductors (e.g., 148 in FIG. 7) running between the cables 150 on the pressure plate assemblies 118 and the electronic module 30. Similarly, an electrical cable 194 connects the electrical motor housing 22 (FIG. 4d) to the electronic module 30 via a second multipin connector 196 and second mating plug 198.

Referring again to FIGS. 1 and 2, the functions of the electronic module 30 will now be discussed. While the description refers primarily to the preferred embodiment of the invention, it is to be understood that the description, with certain modifications, is also applicable to other possible embodiments of the invention.

The electronic module casing 114 (FIG. 3) houses, in part, one or more electronic circuit packs 52 and the rechargeable power supply 32, the latter including four or more AA batteries 166 and the energy pickup coil 116. The electronic circuit packs 52 contain the various units shown in FIG. 1, including the control system 28, energy storage device 34, cardiac pacer unit 36, cardioverter/defibrillator 38, biological recorder 40, and alarm device 42.

The control system 28 may utilize a variety of sensing strategies to provide optimal mechanical pumping assistance in any of three basic modes: normal left ventricular assist mode, ventricular arrhythmia/asystole mode, and failsafe/standby mode. During normal assist mode, the pressure plate assemblies 118 assist in ventricular compression as needed to maintain sufficient blood flow. In the event of ventricular tachycardia, ventricular fibrillation, or asystole, cardioversion/defibrillation or pacing is attempted, as appropriate. Should cardioverting/defibrillating energy be needed, the pressure plate assemblies 118 would first compress the heart 102 so as to eject blood from the organ and thereby decrease the cardioversion/ defibrillation energy threshold. If this electrical therapy is unsuccessful, the pumping mechanism 20 responds by compressing the left ventricle 12 at a rate of approximately 72 beats per minute and with sufficient compression depth to maintain systolic pressure of about 90–120 mmHg. In failsafe mode, the pressure plate assemblies 118, in response to failure of the implanted system, would permit natural movement of the heart 102; the manual pumping mechanism 44 could then be used, if needed, by the patient user or a bystander.

The control system 28 utilizes input from a variety of sensors. For example, data from rate-sensing electrodes 152 (FIG. 7) or 154 (FIG. 2a) enable the control system to coordinate pressure plate compressions with R-waves and to provide A-V synchrony for optimized blood flow, if desired. Typically, three Hall-effect sensors (not shown) in the brushless DC motor 24, in combination with the motor's eight magnets, may be used to determine the position of the pressure plate assemblies 118 by sensing rotation of the motor's rotor, which can be translated into linear displacement of the roller screw's reciprocating shaft 172. Alternatively, exact displacement of the reciprocating shaft 172 can be determined by integrating the angular velocity of the rotor, which is directly proportional to the back electromotive force (EMF) of the motor 24. The pressure plate closing velocity and force also can be readily controlled, if desired, by varying the torque of the motor 24 by a servo mechanism 24s (shown schematically in FIGS. 2a and 4d).

By analyzing such information the control system 28 can calculate and adjust such variables as ejection fraction, aortic blood pressure, stroke volume (cc/beat), and blood flow rate (cc/sec). For example, the heart 102 may be allowed to fill to any left ventricular end diastolic volume, depending on left atrial venous return. Then, based on plate position data, the current of motor 24 can be adjusted to obtain a fixed final ejection position (end systolic volume) in the compression stroke. As another option, a fixed current can be applied for a given time to the motor 24, which results in a fixed torque and force to the pressure plate assemblies 118. This will result in variable end compression positions, depending, for example, on filling time and volume. On the other hand, varying levels of force can be applied to the pressure plate assemblies 118, with sensors then reading the resultant blood pressures and enabling the control system 28 to adjust the force or the end pressure plate position to maintain a programmed aortic blood pressure. Aortic root blood pressure may be sensed using a solid-state pressure transducer (not shown) positioned in the aortic wall. As yet another approach, over a specified number of beats pressure plate work can be gradually added, as a supplement to natural heart function, until aortic systolic pressure reaches a preprogrammed level. Using servocontrol techniques, the amount of pressure plate assistance will automatically adjust to the level required by the natural heart 102 to maintain the desired aortic pressure. Stroke volume can also be assessed by measuring impedance across the electrodes 144, since impedance is related to blood volume within the heart 102.

The control system 28 also contains various automatic self-test features. For example, each time the energy storage device 34 supplies energy to the motor 24 for assisting blood circulation or to the cardioverter/defibrillator unit 38 for tachyarrhythmia conversion, the internal voltage of the batteries 166 is compared to a threshold value in a battery test circuit 54 (FIG. 1). If the battery voltage drops below the threshold value, the battery test circuit 54 enables the patient alarm 42, which may utilize a piezoelectric crystal to produce an audio tone. The patient alarm 42 can also be enabled each time a tachyarrhythmia is detected by the control system 28, thereby warning the patient that he is about to receive a defibrillation or cardioversion pulse.

The control system 28 also includes a real-time electrophysiology/hemodynamic (EH) evaluation mode circuit 56. The EH mode, in which arrhythmia detection by the bipolar electrodes 144 and 152 (FIG. 7) and/or 154 (FIG. 2a) is inhibited, is initiated by command from the programmer 48. The cardiac pacer unit 36 then is placed into the VVT mode (i.e., ventricular pacing, ventricular sensing, pulse triggered by sensed event), but with standard electrophysiology equipment providing simulated R-waves to the programmer 48 via a telemetry link. During this mode, the internal recorder 40 also transmits electrocardiogram (ECG) data, ventricular motion data, and blood flow rate data to the programmer 48. By using the EH mode, the patient's risk of arrhythmia genesis and the most effective treatment modes can be determined, and pumping settings of the ventricular assist device 10 can be adjusted to reduce energy requirements and optimize blood flow and/or pressure.

The cardiac pacer unit 36, cardioverter/defibrillator unit 38, and biological recorder 40, as well as the energy storage device 34, are of types known to those skilled in the art. The cardiac pacer unit 36 is noninvasively programmable, has automatic gain control of the input stages, and provides ventricular, atrial, dual chamber, and antitachycardia pacing as required. The cardioverter/defibrillator unit 38 is noninvasively programmable, has automatic gain control, and is energized from the energy storage device 34 to provide synchronized defibrillation or cardioversion pulses as required.

The cardiac pacer 36 and cardioverter/defibrillator 38, in conjunction with the control system 28 and signals from the cardiac electrodes 144 and 152 of the pressure plate pumping assemblies 118 and from the atrial cardiac electrodes 154, typically diagnose tachyarrhythmias using three criteria: rate, morphology, and rate acceleration. (Additional detection parameters can include rate stability and sustained high rate.) For this purpose, a rate-detection circuit 58 (FIG. 1) of the control system 28 counts the R-waves as detected by the bipolar electrodes 152, for example, and compares this rate with two or more programmed rate thresholds. A morphology-detection circuit 60 examines the shape of transcardiac signals sensed by rectangular electrodes 144 and determines when an absence of isoelectric time occurs, which is characteristic of tachyarrhythmias. Further, an acceleration-detection circuit 62 compares the rate of change of the heart rate with a programmed threshold, rapid acceleration normally being associated with treatable tachyarrhythmias. For example, during exercise-induced sinus tachycardia, rate accelerates typically at 20 beats per minute per second, whereas spontaneous ventricular tachycardia typically results in a rate acceleration of about 90 beats per minute per second. Tachyarrhythmias can also be detected by motion sensors because, for example, the ventricle 12 will quiver rather than contract rhythmically during ventricular fibrillation. Combinations of these criteria identify various types of arrhythmic conditions, and for each type an individual treatment sequence can be programmed into the control system 28. Also, in the event of ventricular arrhythmias that cannot be controlled by the arrhythmia-control units 36 and 38, the control system 28 can be programmed to revert to an asynchronous ventricular assist mode to ensure adequate, or at least life-supporting, blood flow.

Bradycardia diagnosis may be accomplished using signals from the atrial bipolar electrodes 154 (FIG. 2a) and ventricular bipolar electrodes 152 (FIG. 7) on a beat-by-beat basis. Other rate responsive physiological signals may also be used. These signals include venous blood temperature, oxygen content of the blood, blood pH, respiration rate, muscle activity, and QRS duration. If the heart 102 goes into bradycardia and pacing is required, one optional control mode could be to have the pacer 36 search for the optimum pacing rate as determined by measuring cardiac output versus rate.

Output pulses to the heart 102 from the cardiac pacer unit 36 are typically in the microjoule energy range and are at rates typical of cardiac pacing (60–120 pulses per minute) for bradycardia, or at very high rates (150–1500 pulses per minute) to treat tachyarrhythmias. Output pulses from the cardioverter/defibrillator unit 38 are typically in the range of 0.1 joules to 50 joules, and are either asynchronous or synchronous with the R-wave. In the event cardioversion/defibrillation is required, the control system 28 would ensure full compression of the pressure plate assemblies 118 before countershock delivery, thereby minimizing the volume of blood in the heart and achieving a lower cardioversion/defibrillation energy threshold.

The internal biological recorder 40 records and stores electrogram events, such as tachyarrhythmia onset and conversion; device status, such as battery condition; ventricular motion; and blood flow rate. The recorder 40 may utilize a delta-modulation scheme to achieve analog-to-digital conversions of the signals at a typical bit/second rate of 200. The delta-modulated data can then be stored, for example, in a CMOS RAM. On command of the programmer unit 48, the recorder 40 then can delta-demodulate the stored data to produce an analog voltage which can be transmitted to the interrogation unit 50 by way of a telemetry link 64. The recorder 40 can telemeter on-line data as well as stored data, if desired.

The batteries 166 of the internal rechargeable power supply 32 may be four or five lithium/molybdenum/disulfide rechargeable "AA" cells (in series), such as those available from Moli Energy Limited of Vancouver, British Columbia, Canada. The typical characteristics of each battery 166 are as follows:

| | |
|---|---|
| Ampere-hour capacity | 0.7 A |
| Average voltage | 2.0 V |
| Watt-hour capacity | 1.4 W |
| Weight | 20 grams |
| Volume | 8 cc |

Some of the important advantages of the batteries 166 over nickel cadmium batteries normally used in ventricular assist devices include an increased energy density (by a factor of about 2.5); weight reduction from 200 grams to 801 $\propto$ 100 grams; lower internal impedance, resulting in less power loss; higher voltage per cell; an increase in energy retention by a factor of about four (10% per month versus 40% per month at body temperature), which significantly enhances system efficiency; and a reliable state-of-remaining-capacity indicator (cell voltage), whereas there is no indicator for nickel cadmium cells. The absence of an indicator could result in sudden unanticipated device shutdown, placing the patient at risk. Using cell voltage as the remaining-capacity indicator, the depth of cell discharge is accurately controlled by allowing the cell voltage to vary between two predetermined voltage limits, which in turn allows thousands of charge/discharge cycles to be achieved. This is achieved by monitoring battery voltage continuously from the control system 28, automatically activating a charging circuit (not shown) of the rechargeable power supply 32 when a preset lower voltage is reached, and automatically deactivating the charging circuit when battery voltage reaches a preset upper limit.

To prolong the life of the implanted power supply 32, a closely coupled magnetic circuit (not shown) comprising a movable magnet in a coil of wire can be integrated into the driver arms 122 and 124. This magnetic circuit would convert into electrical energy some of the mechanical work done as the pressure plate pumping assemblies 118 are expanded during the filling phase of the ventricle 12. The electrical energy would then be supplied to the implanted rechargeable batteries 166. Further, power lost through truncation of cardioversion/defibrillation pulses, which is required for effective ventricular tachyarrhythmia conversion, can be returned to the rechargeable batteries 166 using power MOSFETS instead of SCRs in the output circuits of the cardioverter/defibrillator unit 38.

The highly efficient batteries 166, combined with the high efficiency of the ventricular assist device 10, permit the internal power supply 32 to operate the implanted device at nominal blood flows for hours before requiring recharging. Further, because the batteries 166 do not off-gas, they can be hermetically sealed within the electronic module's titanium case 114 for enhanced long-term reliability. Thus, the patient's vest- or tether-free time is significantly increased, with a corresponding increase in quality of life.

Referring again to FIG. 1, the functions of the transcutaneous power supply 46 and the programmer/interrogation units 48, 50 will now be further described. The external transcutaneous power supply 46 comprises about 15 power cells (not shown), such as the batteries 166, in a "C" configuration connected in series. The external power supply 46, which weighs about two pounds and is worn by the patient in a belt or vest (not shown), keeps the internal power supply 32 fully charged while providing power for the internal subsystem 14 for at least 10 hours without recharging. At nominal conditions, the transcutaneous power supply 46 can operate the internal subsystem 14 up to a day before being recharged or replaced with a fully charged new power supply belt or vest.

Transcutaneous energy transmission from the external power supply 46 to the internal power supply 32 is accomplished by two inductively coupled concentric coils, one of which is a primary coil (not shown) in the external power supply, and the other of which is the pickup coil 116. The latter, secondary coil may be hermetically sealed within the electronic module case 114 (as outlined in FIGS. 3a and 3b) or may be implanted separately, protected by a butyl rubber coating which is then encapsulated in a polyether-based elastomeric urethane. Energy transmission to the secondary coil 116 can typically be performed at 150 KHz. Because of the large surface area for transcutaneous power transmission, the resulting electromagnetic radiation to the patient's tissue is low — in the range of the earth's magnetic field.

A telemetry link 66 permits noninvasive programming and interrogation of the internal subsystem 14, with communication from the programmer 48 to an internal device 68 in the control system 28 being accomplished with a digital radio frequency (RF) technique. Communication from the internal device 68 to the programmer 48 can be by either an RF channel or an audio channel, the latter using a piezoelectric speaker (not shown). Communication on either channel can be digital for data transmission, or analog for transmission of real-time or recorded electrocardiograms, for example.

In the event of battery depletion or failure of the assist system 14, 16, the manual pumping mechanism 44 may be employed to maintain blood flow. As is shown in FIGS. 2a and 2b, the mechanism 44 includes, in addition to the push button 108, a cylindrical housing 70 and an annular flange 72 for maintaining the position of the housing. The annular flange 72 is connected to the elastomeric tube 182 (FIG. 2b) of the fluid coupling between the paired bellows 180 (FIG. 4d) and 184 (FIGS. 4a, b and c) by a similar flexible plastic tube 74. The push button 108 may be biased outward by, for example, a coil spring (not shown). When the push button 108 is depressed, pressure is exerted on the fluid in the tubes 74 and 182, and thus on the bellows 184 in the actuator housing 128 (FIG. 4a). This in turn engages the driving wedge 186 and wedge followers 132, causing the pressure plate assemblies 118 to compress the ventricle 12. It should be understood that other manual pumping designs are possible; for example, in the absence of a fluid coupling system, the push button 108 may be connected to a flexible drive rod.

The ventricular assist devices 10-10''' in accordance with the invention are considered advantageous in that each normally should be capable of supporting full cardiac output, if necessary. Each device 10-10''' is capable, for example, of supporting a failed left ventricle 12-12''' with a continuous output of 7-10 liters per minute without having to exceed a pump rate of 120 beats per minute into a mean arterial pressure of 120 mmHg (which might be associated, typically, with a peak arterial pressure of 150 mmHg) and a maximum filling pressure of about 15 mmHg. In addition, the rate of pressure rise and fall due to pumping assistance will be low enough to avoid excessive blood turbulence, hemolysis, or blood cavitation. Furthermore, the pressure plate assemblies 118-118''' or resilient bands 300-300', which are external to the ventricular cavities of the heart 102-102''', do not impede venous return, compromise any organ system, or degrade blood circulation in the coronary arteries. The devices 10-10''' also eliminate the need, present in certain prior known ventricular assist devices, for a separate compliance chamber (displaced volume compensation for cycle changes in volume between pumping sacs and encapsulating shells), which may be compromised by fibrous tissue encapsulation and which requires periodic replacement of gas which has diffused through the compliance chamber materials. The invention also eliminates the need for any valves, which have inherent and well-documented problems in prior known cardiac assist devices.

Each of the ventricular assist devices 10-10''' is also advantageous in that it reduces the total weight of all implanted components, when compared to the total weight of known prior art ventricular assist devices. The overall weight of the components, including batteries 166, is in a range of 400-500 grams, which represents a weight reduction by a factor of four from known prior art systems that generally weigh 1500-2000 grams.

Another advantage of ventricular assist device 10 is that the fluid coupling between the bellows 180 and 184 constitutes a failsafe mechanism whereby the pumping mechanism 20, in the event of motor failure, does not restrict the natural movement of the heart 102. Additionally, several embodiments of the invention would permit separate implantation of the motor housing 22, with only the pumping mechanism 20 implanted adjacent the heart. Furthermore, for all ventricular assist devices 10-10''', the electronic module 30 need not be implanted near the pumping mechanism 20-20', but may be remotely implanted. This modular construction facilitates replacement of components, should any fail, and also allows flexibility in determining the optimum implant sites for the individual patient's physiology.

In summary, new and improved biocompatible ventricular assist and arrhythmia control devices 10-10''' have been disclosed. For example, device 10 can be completely and readily implanted in the body of a patient user, eliminating the need for tethering to an external power supply; is of relatively simple, light-weight, and compact construction; requires only a small amount of energy for reliable operation over an extended period of time; incorporates a control mechanism for determining left ventricular stroke volume and for changing compressive force, as needed, to assure an adequate supply of oxygenated blood; and includes bradycardic and tachyarrhythmic control features, which will facilitate device operation in synchronism with left ventricular contraction. In addition, the rechargeable power supply 32 of the device 10 can be readily recharged transcutaneously, and the device can be noninvasively programmed and interrogated. The device 10 places no foreign, nonbiological materials in contact with the blood flow, thereby avoiding the documented danger of clotting and associated body malfunctions. The device 10 also is capable of providing effective mechanical circulatory support to the ventricle 12 of the heart 102 while myocardial function recovers postoperatively.

It is intended that all matter contained in the above description and shown in the accompanying drawings be interpreted not in any limiting sense, but as demonstrative. It is also to be understood that the following claims are intended to cover all of the generic and specific features of the invention.

We claim;

1. A ventricular assist device which can be implanted in patient user exterior to the heart adjacent at least one heart ventricle and which comprises:
   a pumping means which includes one or more movable ventricle compression assemblies adapted for engaging an outer surface of the at least one heart ventricle;
   operating means for cyclically actuating the one or more compression assemblies, such that a ventricle is, first, compressed to aid blood ejection therefrom, and second, released to permit refilling, the operating means including an electrical motor assembly connected to the one or more compression assemblies and including a rotary-to-axial drive-converting mechanism which includes a rotatable member and a reciprocating member driven axially by rotation of the rotatable member;
   control means for regulating actuation of the operating means and enabling cyclical operation of the electrical motor assembly; and
   an electrical power source.

2. The ventricular assist device as recited in claim 1, in which the one or more movable ventricle compression assemblies are actuated by axial movement of the reciprocating member of the rotary-to-axial drive-converting mechanism.

3. The ventricular assist device as recited in claim 2, in which the one or more movable ventricle compression assemblies each includes a pressure plate mounted on a compressive arm via an axle/bearing mount such that the pressure plate is adapted to follow the natural movement of the heart.

4. The ventricular assist device as recited in claim 1, in which the electrical motor assembly is contained within a motor assembly housing that is replaceable separate from the pumping means.

5. The ventricular assist device as recited in claim 4, in which:
the electric motor assembly actuates the one or more movable ventricle compression assemblies of the pumping means by way of a fluid-filled coupling system; and
the fluid-filled coupling system includes separate reciprocating means, one in the electrical motor assembly and one in a pumping means housing, with the separate reciprocating means being connected by elastomeric tubing.

6. The ventricular assist device as recited in claim 5, wherein the separate reciprocating means are first and second bellows.

7. The ventricular assist device as recited in claim 5, wherein the separate reciprocating means are rolling diaphragms.

8. The ventricular assist device as recited in claim 1, in which each of the one or more ventricle compression assembly includes a metal pressure plate connected to the operating means.

9. The ventricular assist device as recited in claim 8, in which the metal pressure plate is formed of a nickel or titanium alloy.

10. A cardiac compression assembly which is intended for use in a cardiac assist device and which includes:
a pressure plate;
a contact pad mounted on the pressure plate for gluing and/or suturing the pressure plate to at least one cardiac chamber; and
mounting means for mounting the pressure plate in a cardiac assist device.

11. The cardiac compression assembly as recited in claim 10 which further includes electrodes means for sensing cardiac signals, transmitting said signals along one or more insulated electrical conductors, and/or delivering heart pacemaker or cardioverter/defibrillator pulses to the heart.

12. The cardiac compression assembly as recited in claim 11, which further includes a cable that contains the one or more electrical conductors and that is itself mounted on said pressure plate.

13. The cardiac compression assembly as recited in claim 10, in which the pressure plate is formed of titanium or platinum alloy.

14. The cardiac compression assembly as recited in claim 10, in which the contact pad is formed of reinforced soft, electrically insulating material.

15. The cardiac compression assembly as recited in claim 14, in which the thickness of the contact pad is progressively reduced toward its periphery to avoid edge stress.

16. The cardiac compression assembly as recited in claim 14, in which the contact pad is formed of silicone rubber reinforced with DACRON (polyester) fibers having a durometer in a range of the order of 30–50.

17. A ventricular assist device which can be implanted in a patient user exterior to the heart adjacent at least one heart ventricle and which comprises:
a pumping means which includes one or more movable ventricle compression assemblies adapted for engaging an outer surface of the at least one heart ventricle;
operating means for cyclically actuating the one or more compression assemblies, such that a ventricle is, first, compressed to aid blood ejection therefrom, and second, released to permit refilling;
control means for regulating actuation of the operating means, the control means including control circuitry disposed in an electronic module which is capable of subcutaneous implantation such that circuitry contained in said electronic module can be both programmed and interrogated transcutaneously;
an electrical power source; and
a casing, said electronic module and said electrical power source being disposed in said casing;
said control circuitry being connected to the pumping means and/or to the operating means by electrical conductor means insulated within implantable electrical cable means; and
said electrical power source being connected to the operating means by implantable electrical cable means.

18. The ventricular assist device as recited in claim 17, which further includes electrode means mounted adjacent at least one of the one or more ventricle compression assemblies, for sensing cardiac electrical signals and transmitting said signals to the control means via the conductor means.

19. The ventricular assist device as recited in claim 18, in which the electrode means is formed of titanium wire mesh or platinum alloy mesh.

20. The ventricular assist device as recited in claim 18, which further includes electrode means adapted to be mounted on at least one heart ventricle, circuitry for producing heart cardioverting/defibrillating pulses and electrical conductor means connected to the electrode means for applying said pulses to the electrode means mounted on said at least one heart ventricle.

21. The ventricular assist device as recited in claim 20, in which, prior to cardioverting/defibrillating pulse delivery, the control means causes the operating means to close each of the one or move movable ventricle compression assemblies, to remove blood from the heart and lower the cardiac cardioversion/defibrillation energy threshold.

22. The ventricular assist device as recited in claim 20, in which said hear cardioverting/defibrillating pulse electrode means and electrical conductor means also are said cardiac electrical signal sensing electrode means and electrical conductor means.

23. The ventricular assist device as recited in claim 18, in which:
the cardiac electric signal transmitting electrical conductor means is contained within additional electrical cable means mounted adjacent respective ones of the one or more ventricle compression assemblies having said sensing electrode means; and
said additional cable means is connected with the control means via a portion of said first-mentioned electrical cable means.

24. The ventricular assist device as recited in claim 18, which further includes servocontrol means for automatically adjusting the torque of motor means to the level required by the natural heart to maintain blood flow.

25. The ventricular assist device as recited in claim 24, which further includes:
first sensing means connected to said cardiac electrical signal sensing electrode means, for sensing measurement of cardiac parameters, including systolic blood pressure, stroke volume, blood flow rate, ejection fraction, cardiac rate, electrocardiogram morphology, and/or cardiac rate acceleration;
second sensing means connected to at least one of the assemblies and operating means, for sensing compression assembly position and/or displacement, and electrical current consumption by the operating means; and
means in said control circuitry for utilizing input from said first and second sensing means to adjust operating parameters of the operating means in accordance with preprogrammed values of the cardiac parameters.

26. The ventricular assist device as recited in claim 14, which further includes electrode means adapted to be mounted on at least one heart ventricle, circuitry for producing heart pacer pulses and electrical conductor means connected to the electrode means for applying said pacer pulses to the electrode means mounted on said at least one heart ventricle.

27. The ventricular assist device as recited in claim 26, in which said pacer pulse electrode means and electrical conductor means also are said cardiac electrical signal sensing electrode means and electrical conductor means.

28. A ventricular assist device which can be implanted in a patient user exterior to the heart adjacent at least one heart ventricle and which comprises:
a pumping means which includes one or more movable ventricle compression assemblies adapted for engaging an outer surface of the at least one heart ventricle, the one or more movable compression assemblies each including a support connected to the operating means and a contact pad on the support for gluing and/or suturing the compression assembly to a ventricle;
operating means for cyclically actuating the one or more compression assemblies, such that the ventricle is, first, compression to aid blood ejection therefrom, and second, released to permit refilling;
control means for regulating actuation of the operating means; and
an electrical power source.

29. The ventricular assist device as recited in claim 28, in which the contact pad is formed of reinforced soft, electrically insulating material.

30. The ventricular assist device as recited in claim 29, in which the thickness of the contact pad is progressively reduced toward its periphery to avoid edge stress.

31. The ventricular assist device as recited in claim 29, in which the contact pad is formed of silicone rubber reinforced with DACRON fibers having a durometer in a range on the order of 30–50.

32. A ventricular assist device which can be implanted in a patient user exterior to the heart adjacent at least one heart ventricle and which comprises:
a pumping means which includes one or more movable ventricle compression assemblies adapted for engaging an outer surface of the at least one heart ventricle;
operating means for cyclically actuating the one or more compression assemblies, such that a ventricle is, first, compressed to aid blood ejection therefrom, and second, released to permit refilling;
control means for regulating actuation of the operating means;
an electrical power source which includes a pack of rechargeable batteries connected to a pickup coil, with the batteries being disposed in a casing capable of subcutaneous implantation such that the batteries can be recharged transcutaneously through the pickup coil; and
implantable electrical cable means connecting the electrical power source to the operating means.

33. A ventricular assist device which can be implanted in a patient user exterior to the heart adjacent at least one heart ventricle and which comprises:
a pumping means which includes one or more movable ventricle compression assemblies adapted for engaging an outer side surface of the at least one heart ventricle and further includes a movable ventricle compression assembly adapted for engaging only an apex of a ventricle;
operating means for cyclically actuating the one or more compression assemblies, such that the ventricle is, first, compressed to aid blood ejection therefrom, and second, released to permit refilling;
control means for regulating actuation of the operating means; and
an electrical power source.

34. The ventricular assist device as recited in claim 33, in which the operating means permits sequential movement of the apex-engaging compression assembly and the side-engaging compression assembly in a ventricle-compressing operation.

35. A ventricular assist device which can be implanted in a patient user exterior to the heart adjacent at least one heart ventricle and which comprises:
a pumping means which includes one or more movable ventricle compression assemblies adapted for engaging an outer surface of the at least one heart ventricle;
operating means for cyclically actuating the one or more compression assemblies, such that a ventricle is, first, compressed to aid blood ejection therefrom, and second, released to permit refilling;
control means for regulating actuation of the operating means; and
an electrical power source including a battery, said control means including circuitry for conducting automatic self tests, such as analysis of remaining battery capacity.

36. A ventricular assist device which can be implanted in a patient user exterior to the heart adjacent at least one heart ventricle and which comprises:
a pumping means which includes one or more movable ventricle compression assemblies adapted for engaging an outer surface of the at least one heart ventricle;
operating means for cyclically actuating the one or more compression assemblies, such that ventricle is, first, compressed to aid blood ejection therefrom, and second, released to permit refilling;
control means for regulating actuation of the operating means; and
an electrical power source, said control means including circuitry for activating a patient alarm in response to malfunction conditions, such as low voltage of a battery in the power source.

37. A ventricular assist device which can be implanted in a patient user exterior to the heart adjacent at least one heart ventricle and which comprises:
- one or more movable ventricle compression assemblies adapted for engaging an outer surface of the at least one heart ventricle;
- automatic operating means for cyclically actuating the one or more compression assemblies, such that a ventricle is, first, compressed to aid blood ejection therefrom, and second, released to permit refilling;
- control means for regulating actuation of the operating means;
- an electrical power source; and
- a manually actuated pump for moving at least one of the movable ventricle compression assemblies to compress said ventricle.

38. A ventricular assist device which can be implanted in a patient user exterior to the heart adjacent at least one heart ventricle and which comprises:
- a pumping means which includes one or more movable ventricle compression assemblies adapted for engaging an outer surface of the at least one heart ventricle;
- operating means for cyclically actuating the one or more compression assemblies, such that a ventricle is, first, compressed to aid blood ejection therefrom, and second, released to permit refilling;
- control means for regulating actuation of the operating means;
- sensing circuitry which forms part of the control means and which is capable of detecting a malfunction in the device and/or the heart;
- an alarm which is responsive to said malfunction-sensing circuiting; and
- an electrical power source.

39. The ventricular assist device as recited in claim 38, in which said electrical power source is implantable in the patient user and said alarm is responsive to device malfunction conditions such as low voltage of a battery in the implanted electrical power source.

40. A ventricular assist device which can be implanted in a patient user exterior to the heart adjacent at least one heart ventricle and which comprises:
- a pumping means which includes one or more movable ventricle compression assemblies adapted for engaging an outer surface of the at least one heart ventricle;
- operating means for cyclically actuating the one or more compression assemblies, such that a ventricle is, first, compressed to aid blood ejection therefrom, and second, released to permit refilling;
- control means for regulating actuation of the operating means;
- means for recording data produced during the operation of said ventricular assist device, the recording means being implantable and capable of transcutaneous interrogation; and
- an electrical power source.

41. A ventricular assist device which can be implanted in a patient user exterior to the heart adjacent at least one heart ventricle and which comprises:
- a pumping means which includes one or more movable ventricle compression assemblies adapted for engaging an outer surface of the at least one heart ventricle;
- operating means for cyclically actuating the one or more compression assemblies, such that a ventricle is, first, compressed to aid blood ejection therefrom, and second, released to permit refilling;
- control means for regulating actuation of the operating means;
- an electrical power source;
- a rigid support member adapted to be positioned external to the heart; and
- at least one resilient band having an intermediate portion surgically implantable in an interventricular wall of the heart, the band having opposite ends which connect to the rigid support member, with at least one of the movable ventricle compression assemblies for engaging the outer surface of the at least one heart ventricle being positionable between the rigid support member and the interventricular wall implantable intermediate portion of the resilient band.

42. A ventricular assist device which can be implanted in a patient user exterior to the heart adjacent at least one heart ventricle and which comprises:
- a pumping means which includes one or more movable ventricle compression assemblies adapted for engaging an outer surface of the at least one heart ventricle, the pumping means also including at least one resilient band having an intermediate portion surgically implantable in an interventricular wall of the heart and having end portions fixed to two movable ventricle compression assemblies such that actuation of the compression assemblies constricts the at least one resilient interventricular wall-implanted band and thereby compresses a ventricle;
- operating means for cyclically actuating the one or more compression assemblies, such that said ventricle is, first, compressed to aid blood ejection therefrom, and second, released to permit refilling;
- control means for regulating actuation of the operating means; and
- an electrical power source.

43. The ventricular assist device as recited in claim 26, which also includes circuitry for initiating a real-time electrophysiology/hemodynamic (EH) evaluation mode in which the pacer circuitry is placed into VVT mode (ventricular pacing, ventricular sensing, pulse triggered by sensed event).

* * * * *